United States Patent
Hawe et al.

[11] Patent Number: 5,100,660
[45] Date of Patent: Mar. 31, 1992

[54] THICKENED ACIDIC AQUEOUS COMPOSITIONS USING CROSS-LINKED

[75] Inventors: Malcolm Hawe; David Farrar, both of West Yorkshire, England

[73] Assignee: Allied Colloids Limited, England

[21] Appl. No.: 512,778

[22] Filed: Apr. 20, 1990

[30] Foreign Application Priority Data

Apr. 21, 1989 [GB] United Kingdom ............. 8909095.5

[51] Int. Cl.$^5$ ................ C08L 33/08; C08L 33/10; A61L 2/18
[52] U.S. Cl. .................. 424/78.35; 424/501; 424/405; 523/122; 524/460; 524/555; 252/106; 252/136; 252/142; 252/547; 252/173; 252/174.23; 422/12
[58] Field of Search ............. 424/78, 81, 501, 405, 424/409; 523/122

[56] References Cited

U.S. PATENT DOCUMENTS

| | | | |
|---|---|---|---|
| 4,172,066 | 10/1979 | Zweigle et al. | 524/829 |
| 4,720,346 | 1/1988 | Flesher et al. | 523/322 |
| 4,737,541 | 4/1988 | Stavenger et al. | 526/303.1 |
| 4,748,220 | 5/1988 | Hartman et al. | 526/312 |
| 4,806,345 | 2/1989 | Bhattacharya | 424/78 |
| 4,892,916 | 1/1990 | Hawe et al. | 526/304 |

Primary Examiner—Thurman K. Page
Assistant Examiner—E. Webman
Attorney, Agent, or Firm—Ostrolenk, Faber, Gerb & Soffen

[57] ABSTRACT

This invention relates to aqueous acidic solutions which are thickened by cationic polymer, the polymer being added to the solution in the form of particles below 10 μm in size. The useful cationic polymers are formed from a water soluble cationic ethylenically unsaturated monomer or blend of monomers comprising dialkylaminoalkylacrylics that includes a polyethylenically unsaturated cross-linking agent. A peak viscosity is achieved in the aqueous acidic solution at a particular cross-linker concentration.

The concentration of cross-linking agent chosen is carefully controlled so that the viscosifying effect can be optimised whilst minimising the amount of polymer that has to be added. The amount of polymer in the aqueous acidic solution is typically in the range of from, 0.01% to 5% dry weight polymer.

16 Claims, 2 Drawing Sheets

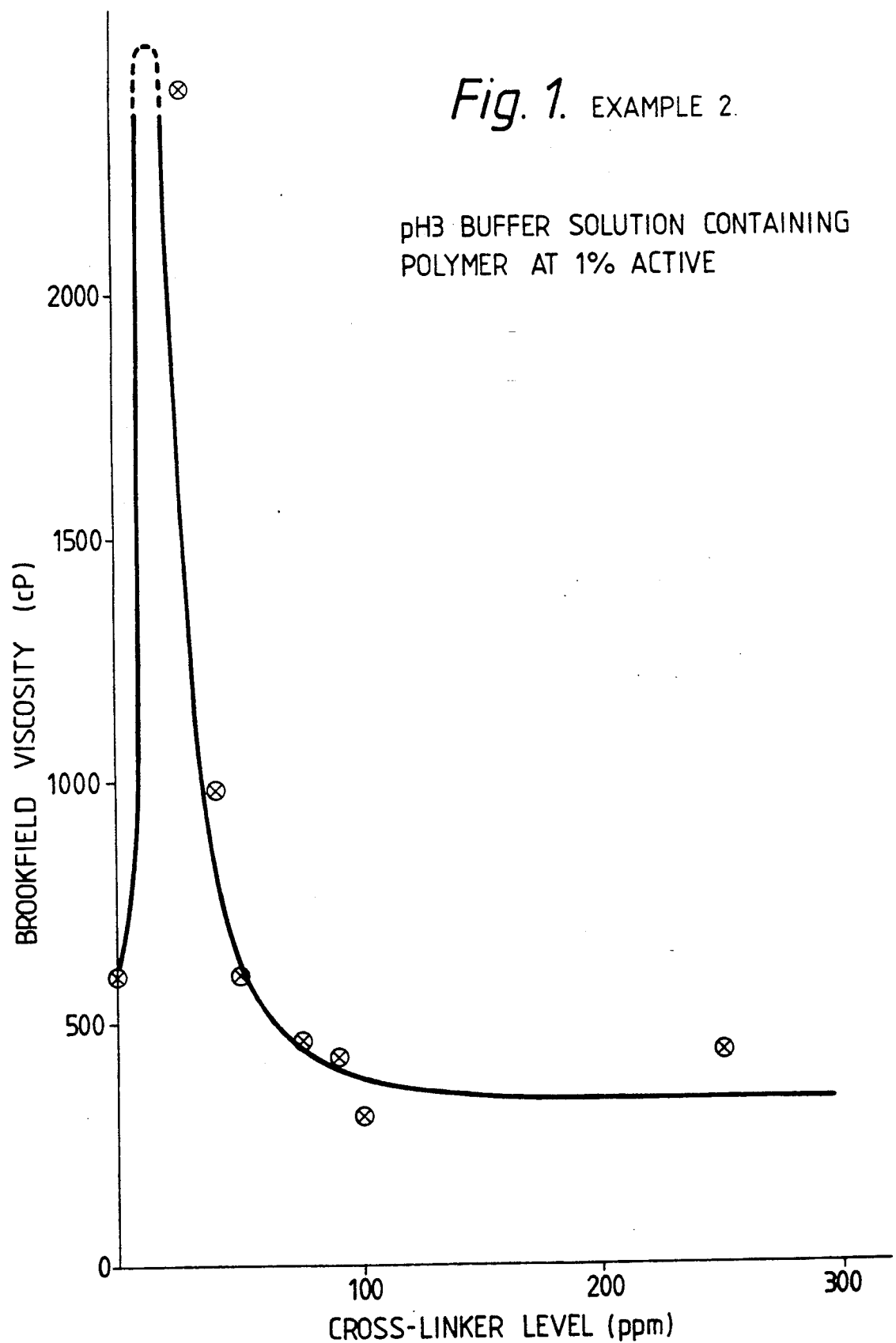

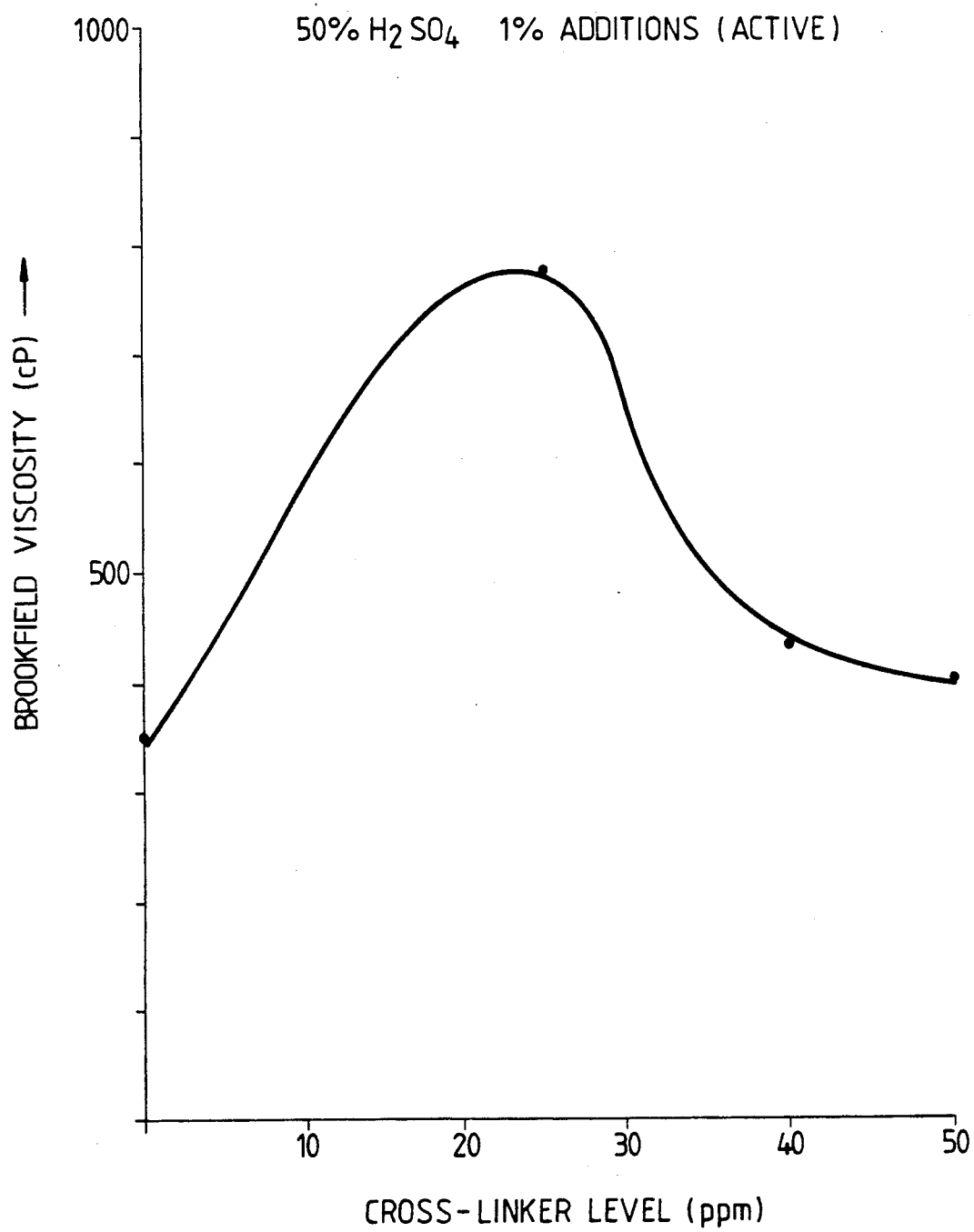
Fig. 2. EXAMPLE 3.

THICKENED ACIDIC AQUEOUS COMPOSITIONS USING CROSS-LINKED

It is standard practice to thicken the aqueous phase of aqueous compositions by dissolving in the aqueous phase a water soluble polymeric thickening agent. This material may be a natural or modified natural polymer, for instance hydroxy ethyl cellulose, or it maybe a synthetic polymer, for instance polyacrylic acid. The polymer is usually intended to be wholly soluble in the aqueous phase and if the polymer is synthetic then it is substantially wholly linear.

These thickeners give satisfactory results when the aqueous solution is relatively free of electrolyte and when it is not subjected to shear. In U.S. Pat. Nos. 4,059,552 and 4,172,066 it is described that aqueous compositions whose viscosity is relatively resistant to shear can be obtained by using, as thickener, microbeads of a water insoluble, water swellable polymer formed by cross-linking water soluble monomer. In U.S. Pat. No. 4,059,552 the amount of cross-linking agent is stated to be 50 to 1000 ppm and the aqueous medium can contain sodium chloride. In U.S. Pat. No. 4,172,066 there is a similar disclosure of thickeners but there are examples of reducing permeability of an underground formation by the use of an anionic polymer cross-linked with various amounts of cross-linking agents. Although all the examples in U.S. Pat. No. 4,059,552 and U.S. Pat. No. 4,172,066 use an anionic polymer, a variety of monomers are described in U.S. Pat. No. 4,172,066 for the formation of the polymers, including various cationic monomers.

In U.S. Pat. No. 4,806,345, personal care compositions are described which include a cosmetically active ingredient in an aqueous base that is thickened by a lightly cross-linked cationic vinyl addition polymer. The compositions are intended for application to the body for cosmetic purposes. The preferred amount of cross-linking agent is from 50 to 500 ppm based on monomer. It seems probable that the cationic thickening agent is preferred because it will be compatible with the normal materials in the cosmetic compositions and may tend to render the composition more substantive to the skin or hair.

It is known to thicken a downhole acidizing solution by use of linear water soluble cationic polymer (for instance as described in GB 2,110,744). However the compositions have a stringy rheology that is unsatisfactory for many cationic compositions. The use of cationic reverse phase polymers cross-linked by the typical amounts used in U.S. Pat. No. 4,059,552 (for instance 100 to 500 ppm cross-linker) eliminates the stringiness and can give very high viscosity at above a critical concentration but only low viscosification at lower concentrations. For many purposes it would be desirable to thicken an aqueous electrolyte in such a manner that a useful increase in viscosity is achieved at relatively low polymer amounts to give a rheology that is not very stringy but which will form, for instance, a viscous film when flowing over a hard surface.

The use of non-ionic or anionic thickener, for instance hydroxyethyl cellulose, polyacrylamide or sodium polyacrylate, in linear, soluble form is unsatisfactory for thickening aqueous cationic electrolyte solutions because interaction with the cationic electrolyte causes inadequate viscosity, even at high polymer concentration, and may cause precipitation.

At present it is impossible to thicken many aqueous cationic electrolyte solutions to give an optimum combination of viscosity and rheology at relatively low polymer concentrations.

It would be desirable to be able to provide an effective thickener for a range of aqueous acidic compositions, and in particular provide such a thickener that could be used at low concentrations to give convenient rheology.

An aqueous acidic solution according to the invention is thickened by a cationic polymer that is added to the solution in the form of particles below 10 μm in size and that is formed from a water soluble cationic ethylenically unsaturated monomer or blend of monomers that includes a polyethylenically unsaturated cross-linking agent that provides a peak viscosity in the aqueous acidic solution at a cross-linker concentration within the range 5 to 45 ppm, and in which the amount of cross-linker is within 33% of the amount that gives the peak viscosity. (In this specification "acidic" means pH less than 7.)

BRIEF DESCRIPTION OF THE DRAWINGS

FIG. 1 is a graph plotting the viscosity against the amount of cross linker as described in Example 2, and FIG. 2 is a graph plotting viscosity against the amount of cross linker as described in Example 3.

The invention is based in part on the surprising discovery that the viscosity imparted to an acidic solution by a cross linked, small particle size, cationic polymer is exceedingly dependent on the precise amount of cross-linking. In particular, the viscosity obtained at any given polymer addition to any given acidic solution will be at some measured value when the polymer is free of cross-linking and as the amount of cross-linking increases the viscosity increases rapidly before falling back again. For all the combinations of acidic solution and cationic polymer that we have examined, we have observed a clear peak in viscosity at some level of cross linker between 5 and 45 ppm. In most instances this peak is in the range 10 to 20 or 25 ppm cross-linker. After passing the peak, the viscosity gradually drops with increasing amounts of cross-linking agent.

In the invention, we select an amount of cross-linking agent that is close to the amount that gives the optimum or peak viscosity in the particular aqueous acid that is being thickened by the particular amount of polymer that is present. This peak can be determined by plotting the viscosity against cross linker level for a range of polymers that differ only in the amount of cross linker. For most purposes the amount of cross linker that is used in the invention is at the peak but of course this is not absolutely essential and useful results can also be obtained slightly above or slightly below the peak. Generally the amount of cross linker is within 33% of the amount that gives the peak viscosity, and most usually is within 20% and usually within 10% of the amount that gives the peak viscosity.

It should be appreciated that the amount of cross linker that gives the peak viscosity will tend to vary from one aqueous acidic solution to another and will also vary according to the other properties of the polymer, such as its method of polymerisation and the monomers from which it was formed.

By selecting the amount of cross linker at the peak viscosity it is possible to optimise the viscosifying effect whilst minimising the amount of polymer that has to be added. Since the amount of polymer can be relatively low this minimises any adverse effects that the polymer might otherwise have on the rheology of the acidic composition. Additionally, since the polymer is cross linked, this greatly reduces the tendency for the polymer to give the composition a stringy characteristic.

By the invention, it is easily possible when using relatively low amounts of polymer to obtain fluid compositions that are acidic and yet which have a very convenient combination of viscosity and rheology properties, for instance so that they will cling and flow over a hard surface (for instance a toilet bowl or other surface that is being cleaned or sterilised) but which does not give a stringy character or set into a relatively rigid gel. In particular it is possible to vary widely the viscosity obtainable from any particular cross-linked polymer by choice of the amount of polymer in that even relatively small amounts of polymer give a useful viscosity increase. This is in marked contrast to traditional cross linked viscosifying agents, such as those exemplified in U.S. Pat. No. 4,059,552, where they give relatively low viscosity increase at low polymer additions but, once a critical polymer concentration is reached, further increase in the polymer concentration gives a very rapid increase in viscosity. Thus there is a tendency that conventional cross-linked polymeric thickeners either give no useful viscosity increase or, if present to give a useful effect, give such a high viscosity that the system will not flow under gravity over a surface.

The polymers can be homopolymers or copolymers and are formed from monoethylenically unsaturated monomer that is either water soluble cationic monomer or is a cationic blend of monomers that may consist of cationic monomer or may consist of a mixture of cationic and non-ionic monomers. If a blend of monomers is being used then part of the blend may have low water solubility providing the total blend is water soluble. The monomers can be allyl monomers but are generally vinyl, preferably acrylic.

Suitable cationic monomers are dialkylaminoalkyl-acrylates and -methacrylates, especially dialkylaminoethyl acrylate, and their quaternary or acid salts, and dialkylaminoalkylacrylamides or methacrylamides and their quaternary or acid salts for instance methacrylamidopropyl trimethyl ammonium chloride and Mannich products such as quaternised dialkylaminomethylacrylamides. Alkyl groups are generally $C_{1-4}$ alkyl.

Suitable non-ionic monomers are acrylamide, methacrylamide, N-vinyl pyrrolidone, and low alkyl or hydroxyalkyl (meth) acrylates. Water insoluble acrylic (or other ethylenically unsaturated) monomers such as methyl methacrylate, styrene or acrylonitrile may be included in sufficiently small amounts that the blend is soluble.

Blends of 0 or 5 to 90%, preferably 10–50%, acrylamide with dialkylaminoalkyl-acrylate or, preferably, -methacrylate as acid addition or quaternary addition salts, or the cationic homopolymers are preferred.

The monomers can contain hydrophobic groups, e.g., as described in EP-A-0172723, for instance on page 10 of that. If the monomer is to impart insolubility to the polymer the ethoxy chain should be short or absent, i.e., n=0. The allyl ether monomers are especially preferred.

The polymer must be added while in the form of particles below 10 μm in size, and preferably below 2 μm in size. These can be made by comminuting cross-linked polymer gel but preferably the particles are formed initially in the cross-linked state. The particles may be added to the aqueous solution as disintegratable aggregates or pellets, but preferably are added as a dispersion in a liquid, generally a non-aqueous liquid such as a hydrocarbon. This dispersion may be made by dispersing preformed particles in the liquid but is preferably made by reverse phase polymerisation of the monomer or monomer blend in the presence of the cross linker.

The monoethylenically unsaturated material may be contaminated with a small amount of cross-linking agent and the amount of additional cross-linking agent that is added will therefore be selected having regard to this. Preferably the monoethylenically unsaturated material is as free of cross-linking agent as is commercially possible, for instance containing cross-linking agent in an amount that gives cross-linking or chain-branching less than is given by 1 ppm MBA (1 part methylene bis acrylamide per million parts monomer). The amount of MBA that is added is at least 5 ppm and below 45 ppm (based on monomer), generally 10 to 40 ppm. The precise amount will depend upon the polymerisation and other processing conditions. Instead of using MBA, cross-linking may be by equally effective amounts of other diethylenically unsaturated compounds such as ethylene glycol di-(meth)acrylate, di-(meth)acrylamide, cyanomethylacrylate, vinyloxyethylacrylate or methacrylate and other means of cross linking, e.g., formaldehyde or glyoxal or metal salt addition. Preferably a water-soluble cross-linking agent is used.

The degree of non-linearity can additionally be controlled by the inclusion of chain-transfer agents in the polymerisation mixture. Their use, in combination with cross-linking agent, will tend to promote chain branching rather than cross-linking. Amounts may vary widely. For instance 1,000 to 5,000 ppm (based on monomer) of a moderate chain-transfer agent such as isopropyl alcohol may be suitable whilst much lower amounts, typically 100 to 500 ppm, of more effective chain branching agents such as mercaptoethanol are useful. Often, however, adequate results are obtained by conducting polymerisation under conventional conditions, without deliberate addition of chain-transfer agent, using commecially pure monoethylenically unsaturated monomer together with the specified amount of MBA or other cross-linking agent.

Preferred polymers are often formed of 0 to 40% acrylamide and 100 to 60% dialkylamino ethyl methacrylate quaternary salt or a copolymer of from 5 to 40% acrylamide and 95 to 60 dialkylaminoethyl methacrylate quaternary salt (for instance 20% acrylamide 80% dimethylaminoethyl methacrylate quaternary salt) cross linked with 10 to 30 ppm MBA or other cross-linker. All parts and percentages are by weight. The precise optimum for any particular composition can be determined by observing the properties of the composition when thickened with the chosen amount of a range of polymers differing from one another solely by differing the amounts of MBA from 5 to 45 ppm.

The amount of polymer is selected for the optimum properties of viscosity and rheology with the minimum amount of polymer and typically may be in the range 0.01% to 5%, often 0.02% to 2%, dry weight polymer based on the aqueous composition.

The polymerisation conditions are preferably such that the polymer has, if uncross linked, a conventional thickener high molecular weight of 5 million to 30 million and an intrinsic viscosity of above 4, preferably above 6, e.g., up to 10 to 15 dl/g. If the polymer is cross linked it is preferably polymerised such that it would have such molecular weight if it had been made in the absence of cross linking agent. However cross-linking will reduce the IV but shearing the polymer solution may then cause the IV to increase, as explained later.

The particle size in the emulsion or reverse phase polymerisation mixture may be controlled by the degree of shear applied to the monomers and by the possible presence of emulsifying agent. Emulsion polymerisation may be utilised when polymerising, for instance, water insoluble monomers such as acrylic esters or water insoluble but acid soluble monomers such as amines (the resultant polymer being distributed into acidic aqueous composition) but generally reverse phase emulsion or suspension polymerisation is utilised when the monomer or monomer blend is soluble in water. The aqueous monomer is emulsified into a suitable non-aqueous liquid, generally in the presence of a water-in-oil emulsifier, generally in an amount below the critical micelle concentration. Emulsifiers, stabilisers, non-aqueous liquids and other reverse phase polymerisation materials and process details are described in, for instance, EP-A-0126528. The polymer particles may be dehydrated, for instance by subjecting the dispersion to azeotropic distillation.

The liquid product resulting from the reverse phase polymerisation or emulsion polymerisation is generally used as such, without separation of the polymer particles from it, but if desired dried polymer particles may be separated from the dispersion in known manner. Because these dry particles will be very dusty they should preferably be formed into pellets that will disintegrate upon addition to water.

The polymer-in-oil emulsion that results from reverse phase polymerisation may be added to the acidic solution to be thickened in the presence of oil-in-water emulsifier in conventional manner.

When, as is preferred, the polymeric material is a copolymer of acrylamide with at least 10%, and preferably at least 50%, by weight dialkylamino alkyl acrylate (generally as acid addition or quaternary ammonium salt) the degree of non-linearity is preferably such that the polymer has an ionic regain (IR) of at least 15%. IR is calculated as $$\frac{x - y}{x} \times 100$$

where x is the ionicity measured after applying standard shear and y is the ionicity of the polymer before applying standard shear.

These values are best determined by forming a 1% composition of the polymer in deionised water, allowing this to age for 2 hours and then further diluting it to 0.1% active polymer. The ionicity of the polymer y is measured by Colloid Titration as described by Koch-Light Laboratories Limited in their publication 4/77 KLCD-1. (Alternatively the method described in BP 1,579,007 could possibly be used to determine y.) The ionicity after shear, x is determined by measuring by the same technique the ionicity of this solution after subjecting it to standard shear.

The shear is best applied to 200 ml of the solution in a substantially cylindrical pot having a diameter of about 8 cm and provided in its base with a rotatable blade about 6 cm in diameter, one arm of the blade pointing upwards by about 45 degrees and the other downwards by about 45 degrees. The blade is about 1 mm thick and is rotated at 16,500 rpm in the base of the pot for 10 minutes. These conditions are best provided by the use of a Moulinex homogeniser but other satisfactory conditions can be provided using kitchen blenders such as Kenwood, Hamilton Beach, Iona or Osterizer blenders or a Waring Blendor.

In practice the precise conditions of shear are relatively unimportant since, provided the degree of shear is of the same order of magnitude as specified, it will be found that IR is not greatly affected by quite large changes in the amount, for instance the duration, of shear, whereas at lower amounts of shear (for instance 1 minute at 16,500 rpm) IR is greatly affected by small changes in shear. Conveniently therefore the value of x is determined at the time when, with a high speed blade, further shear provides little or no further change in ionicity. This generally requires shearing for 10 minutes, but sometimes longer periods, e.g., up to 30 minutes with cooling, may be desired.

The polymers used in the invention preferably have IR above 30%, often in the range 35 to 45%. IR may increase from zero at zero cross linker up to a peak or plateau at a level around, for instance 15 to 25 ppm, cross linker and preferably IR is at or near this peak or plateau, generally at as low a level of cross linking as is consistent with the high IR value.

The acidic medium that is thickened in the invention can be one of a wide range of aqueous acidic solutions, that is to say solutions having a pH of below 7, and generally below 6. Usually the pH is below 4. The solution may be, for instance, a simple acid solution or it may be the continuous phase of a system having emulsified or dispersed particles of organic or inorganic material. Thus the viscosification may act as a dispersion or emulsion or suspension stabilisation effect.

One form of aqueous acid is a mineral acid solution, for instance hydrochloric acid or sulphuric acid. The acid solution may be a downhole acidising solution. It may be a solution for cleaning metal, for instance a rust-removing composition.

It may be an emulsion of, for instance, bitumen or other tar material, for instance to provide a road surfacing emulsion. Such emulsions are stabilised with cationic surfactants, typically fatty imidazolines and a wide variety of other compositions containing fatty imidazolines may be thickened in the invention. Various acidic emulsions and latices of various synthetic polymers may be thickened.

Ceramic and other toilet or domestic cleaners may be thickened, for instance such as those based on citric and/or phosphoric acid, hydrochloric acid with an ethoxylated amine, hydrochloric acid with a mixture of cationic and non-ionic surfactants, and hydrochloric acid blended with phosphoric acid. Such systems may, for instance, be intended to remove lime scale.

The aqueous composition may contain a quaternary ammonium surfactant. Such materials are, for instance, useful as biocides, for instance for agricultural, veterinary, household, industrial or institutional cleansing purposes. Typical quaternary compounds that can be thickened include alkyl dimethylbenzyl ammonium chloride, alkyl dimethylamino betaine and trimethyl coco ammonium chloride, all of which can be used as, for instance, hospital, household, industrial or institutional cleaners.

The following are some examples.

EXAMPLE 1

A reverse phase dispersion was formed by dispersing into a conventional reverse phase non-aqueous liquid containing emulsifying agent and amphipathic stabiliser an aqeuous monomer blend consisting of 80% by weight dimethylaminoethyl methacrylate methyl chloride quaternary salt and 20% acrylamide and 15 ppm methylene bis acrylamide. The mixture was degassed and initiated in the conventional manner and polymerisation was allowed to go to completion. The mixture was then subjected to azeotropic distillation to provide a substantially anhydrous dispersion of polymer particles less than 2 μm in size dispersed in the non-aqueous liquid.

The IR value of this product, when measured as defined previously, is about 40%.

The above process was repeated using different amounts of cross linker ranging from 5 ppm upwards.

EXAMPLE 2

A range of polymers cross linked with, respectively, zero, 25, 40, 50, 75, 90, 100 and 250 ppmMBA were tested as thickeners for a solution buffered to pH 3 by potassium hydrogen phthalate and hydrochloric acid, the polymer addition being at 1%. The Brookfield viscosity was measured in cP at 23° C. The results are shown in FIG. 1 which is a graph plotting the viscosity against the amount of cross-linker. The precise point of the peak is not entirely clear from this plot but clearly is at around 20 ppm and in the invention any amount of cross-linker between 10 and 35 ppm clearly gives a very considerable benefit compared to the uncross linked or more highly cross-linked systems.

EXAMPLE 3

The process of Example 2 was repeated but on a 50% sulphuric acid composition. The results are shown in FIG. 2 which again demonstrates a peak at around 20 to 25 ppm, and clearly there is considerable benefit at cross linker values of from 10 to 35 ppm.

EXAMPLE 4

At 1% polymer addition to phosphoric acid, the linear polymer gave a Brookfield viscosity of 550, the polymer cross-linked with 25 ppm gave a viscosity of 7,300 cP and the polymer cross-linked with 40 ppm gave a viscosity of 1,400 cP.

EXAMPLE 5

A biocide solution was formed containing 5% trimethyl coco ammonium chloride and 1% of various of the polymers was added to it. At the normal shear values associated with a Brookfield viscometer it was found that the highest viscosity was obtained with the polymer having 15 ppm cross linker, the next lowest was from the linear polymer, the next lowest from the polymer cross-linked at 25 ppm and the lowest was from the polymer cross-linked at 75 ppm.

A different order of vicosities was achieved under values of extremely low shear and so it should be understood that the benefits of the invention may occur primarily in those circumstances where slight to moderate shear is to be applied, for instance when a composition is to be applied to a surface as a cleaner.

EXAMPLE 6

Polymers were formed from an 80:20 (wt) mixture of methyl chloride quaternised dimethylamino ethylacylate and acrylamide containing differing amounts of MBA cross linker in the range 0–250 ppm using the same reverse phase method as in Example 1. They were dissolved in deionised water and in a 1 g/l sodium chloride solution at various polymer concentrations and the Brookfield viscosity of the solutions was tested. The results are shown in the following table, which gives the Brookfield viscosities of the solutions (cPs).

| | Concentration of Polymer (% active) | | | | | | | |
|---|---|---|---|---|---|---|---|---|
| | 1.0% | | 0.5% | | 0.25% | | 0.1% | |
| ppmMBA Crosslinker | water | salt soln. | water | salt soln. | water | salt soln. | water | salt soln. |
| 0 | 4400 | 2330 | 1900 | 510 | 450 | 60 | 350 | 30 |
| 5 | 6150 | 4270 | 2630 | 1050 | 1160 | 190 | 440 | 30 |
| 15 | 9350 | 5050 | 3840 | 1600 | 1450 | 100 | 400 | 24 |
| 25 | 12900 | 6500 | 7500 | 1000 | 3000 | 100 | 700 | 20 |
| 50 | 24370 | 8460 | 12320 | 500 | 3750 | 20 | 370 | 5 |
| 75 | 30000 | 7400 | 13800 | 500 | 2800 | 20 | 200 | 5 |
| 250 | 63000 | 6000 | 1360 | 425 | 52 | 10 | 16 | 2 |

The results show that in deionised water at a polymer concentration of 1% increasing the cross linker concentration increases the viscosity which can be achieved even up to a cross linker concentration of 250 ppm MBA. However at a 0.5% polymer concentration the viscosifying power of the polymer increases up to about 75 ppm MBA but with higher amounts of MBA the viscosifying power decreases dramatically. With lower product concentrations the optimum viscosifying effects are achieved at cross linker concentrations which are lower than 75 ppm–for 0.25% the optimum is at about 50 ppm and for 0.1% the optimum is about 20 or 25 ppm MBA. For the 1 g/l sodium chloride solution at 1% polymer concentration a polymer formed with about 50 ppm MBA gives optimum viscosity. At 0.5% polymer concentration optimum viscosity is a lower cross-linker concentration viz about 15 ppm and the optimum cross linker concentration decreases as the polymer concentration decreases.

Optimum thickening is thought to be achieved with cross-linker concentrations and polymer concentrations such that the polymer swells in the liquid to be thickened so that there is effectively no continuous liquid phase between particles which would lubricate the particles allowing them to move past each other to give a low viscosity solution. Increasing the cross-linker concentration reduces the swellability of the particles and in general terms increases the viscosifying power. But at polymer concentrations below the amount which allows all of the liquid phase to be absorbed into the polymer the viscosity drops off dramatically. In electrolyte solutions, such as acidic solutions or solutions of sodium chloride or solutions of polyelectrolytes, the polymers are less swellable and so the optimum viscosifying effects are achieved at lower cross-linker concentrations. At very low polymer concentrations (0.1%) the linear (0 ppm MBA) polymer appears to have as much effect as the 5 ppm MBA polymer.

We claim:

1. An aqueous acidic solution which contains a thickening amount in the range of 0.01 to 5% by weight of a cationic polymer containing a cross linking agent wherein the polymer has been added to the solution while in the form of particles whose size down not exceed 10 μm and wherein the cationic polymer is formed from polymerisable material consisting essentially of water soluble ethylenically unsaturated monomer or blend of monomers comprising 10 to 100% cationic monomer selected from the group consisting of dialkylaminoalkyl(meth)acrylates, dialkylaminoalkyl(meth)acrylamides, the acid salts thereof, and the quaternary salts thereof and polyethylenically unsaturated crosslinking agent and wherein the viscosity of the solution for any given amount of said polymer is both a function of the amount of crosslinking agent in the polymerisable material and the peak viscosity of the solution, said peak occuring when the amount of crosslinking agent is present between 5 and 45 ppm based on monomer(s), and wherein the amount of crosslinking agent in the polymerisable material is within 33% of the amount which causes the solution to have said peak viscosity.

2. An aqueous acidic solution according to claim 1 wherein the cross-linking agent is at a concentration in the range 10 to 25 ppm.

3. An aqueous acidic solution according to claim 1 wherein the amount of crosslinker is within 20% of the concentration that gives the peak viscosity.

4. An aqueous acidic solution according to claim 1 wherein the polymer is added to the solution in the form of particles whose size does not exceed 2 μm.

5. An aqueous acidic solution according to claim 1 wherein the cationic polymer is a homopolymer formed from monoethylenically unsaturated water soluble cationic, monomers.

6. An aqueous acidic solution according to claim 1 wherein the cationic monomers are acrylic monomers.

7. An aqueous solution according to claim 1 wherein the polymer blend comprises 10 to 50% acrylamide and 50 to 90% dialkylaminoalkyl (meth) acrylate as acid addition or quaternary addition salts.

8. An aqueous acidic solution according to claim 1 wherein the cross-linking agent for cross-linking the ethylenically unsaturated monomers is methylene (bis) acrylamide, ethylene glycol di-(meth) acrylate di-(meth)acrylamide, cyanomethylacrylate, vinyloxyethyl(meth) acrylate, formaldehyde, glyoxal or metal salt.

9. An aqueous acidic solution according to claim 1 wherein the intrinsic viscosity of the thickening polymer is above 4 and below 15 dl/g.

10. An aqueous acidic solution according to claim 1 wherein the thickening polymer is added in the presence of an oil-in-water emulsifier to the acidic solution to be thickened as a polymer-in-oil emulsion resulting from reverse phase polymerisation.

11. An aqueous acidic solution according to claim 1 wherein the ionic regain of the thickening polymer is at least 15%.

12. An aqueous acidic solution according to claim 1 having a pH of below 6.

13. An aqueous acidic solution according to claim 1 that is a household, industrial or institutional cleaner or an agricultural or veterinary biocide.

14. In a process for thickening an aqueous acidic solution which comprises adding a thickening amount of a thickening agent thereto, the improvement which comprises the employment as said thickening agent of 0.01 to 5% by weight of particles of a cationic polymer formed from polymerizable material consisting essentially of water soluble monoethylenically unsaturated monomer or blend of monomers comprising 10 to 100% cationic monomer selected from the group consisting of dialkylaminoalkyl(meth)acrylates, dialkylaminoalkyl(meth)acrylamides, the acid salts thereof, and the quaternary salts thereof and polyethylenically unsaturated crosslinking agent, said particles having a size which does not exceed 10 μm, said cationic polymer being such that the viscosity of the resulting solution at a given amount of said polymer is both (a) a function of the amount of crosslinking agent in the polymerizable material and (b) the amount of crosslinking agent which provides the thickened solution with its peak viscosity which amount is between 5 and 45 ppm based on monomer(s), and said crosslinking agent in the polymerizable material being within 33% of the amount that gives said peak viscosity.

15. The process of claim 14 in which the amount of crosslinking agent is in the range of 10 to 25 ppm.

16. The process of claim 14 in which the polymer is added to the solution in the form of particles whose size does not exceed 2 μm.

* * * * *